(12) United States Patent
Danielsson et al.

(10) Patent No.: US 9,993,220 B2
(45) Date of Patent: Jun. 12, 2018

(54) SCATTER ESTIMATION AND/OR CORRECTION IN X-RAY IMAGING

(71) Applicant: PRISMATIC SENSORS AB, Stockholm (SE)

(72) Inventors: Mats Danielsson, Taby (SE); David Michael Hoffman, New Berlin, WI (US)

(73) Assignee: PRISMATIC SENSORS AB, Stockholm (SE)

( * ) Notice: Subject to any disclaimer, the term of this patent is extended or adjusted under 35 U.S.C. 154(b) by 0 days. days.

(21) Appl. No.: 15/505,302

(22) PCT Filed: Oct. 8, 2015

(86) PCT No.: PCT/SE2015/051072
§ 371 (c)(1),
(2) Date: Feb. 21, 2017

(87) PCT Pub. No.: WO2016/209138
PCT Pub. Date: Dec. 29, 2016

(65) Prior Publication Data
US 2017/0265833 A1 Sep. 21, 2017

Related U.S. Application Data

(60) Provisional application No. 62/185,237, filed on Jun. 26, 2015.

(51) Int. Cl.
*A61B 6/00* (2006.01)
*A61B 6/03* (2006.01)

(52) U.S. Cl.
CPC ............ *A61B 6/5282* (2013.01); *A61B 6/032* (2013.01); *A61B 6/4233* (2013.01); *A61B 6/4241* (2013.01); *A61B 6/4291* (2013.01)

(58) Field of Classification Search
None
See application file for complete search history.

(56) References Cited

U.S. PATENT DOCUMENTS 5,821,540 A * 10/1998 Sato .................. G01T 1/242
250/370.06
6,618,466 B1 9/2003 Ning
(Continued)

FOREIGN PATENT DOCUMENTS

| EP | 1469303 A1 | 10/2004 |
|---|---|---|
| KR | 20160025199 A | 3/2016 |
| WO | 03/073377 A2 | 9/2003 |

OTHER PUBLICATIONS

International Search Report, dated Jul. 7, 2016, from corresponding PCT application No. PCT/SE2015/051072.
(Continued)

*Primary Examiner* — Hoon Song
(74) *Attorney, Agent, or Firm* — Young & Thompson

(57) ABSTRACT

Disclosed are methods and devices for estimating object scatter and/or internal scatter in a multi-level photon-counting x-ray detector, as well as x-ray tomographic imaging while correcting for object and internal scatter. The x-ray detector has at least two layers of detector diodes mounted in an edge-on geometry, e.g. designed for 1) estimating the object scatter contribution to the counts in a top layer of the at least two layers based on difference(s) in counts between the top layer and lower layer(s) under the assumption the object scatter has a slowly varying spatial distribution, and/or 2) estimating counts from reabsorption of photons that have Compton scattered inside the detector based on selectively blinding some detector elements from primary radiation by placing a highly attenuating beam stop on top (Continued)

of the detector elements, in lower layer(s) or in both top layer and lower layer(s), and measuring the counts in those detector elements.

25 Claims, 11 Drawing Sheets

(56) References Cited

U.S. PATENT DOCUMENTS

| | | | |
|---|---|---|---|
| 6,953,935 | B1 | 10/2005 | Hoffman |
| 8,183,535 | B2 | 5/2012 | Danielsson et al. |
| 9,488,739 | B2* | 11/2016 | Pelc .................. G01T 1/247 |
| 2002/0018543 | A1* | 2/2002 | Danielsson ........... G01T 1/1644 378/98.8 |
| 2004/0206908 | A1 | 10/2004 | Lange et al. |
| 2007/0133747 | A1 | 6/2007 | Manak et al. |
| 2009/0129538 | A1* | 5/2009 | Tkaczyk ............... A61B 6/032 378/5 |
| 2010/0204942 | A1 | 8/2010 | Danielsson et al. |

OTHER PUBLICATIONS

Bomefalk, H. and M. Danielsson. "Photon-counting spectral computed tomography using silicon strip detectors: a feasibility study." Physics in medicine and biology, vol. 55 (2010): 1999-2022.

Bornefalk, H., M. Persson, and M. Danielsson. "Allowable forward model misspecification for accurate basis decomposition in a silicon detector based spectral CT." IEEE transactions on medical imaging, vol. 34, No. 3 (2015): 788-795.

Roessl, E., and R. Proksa. "K-edge imaging in x-ray computed tomography using multi-bin photon counting detectors." Physics in medicine and biology, vol. 52 (2007): 4679-4696.

Zhu, L, N.R. Bennett, and R. Fahrig. "Scatter correction method for x-ray CT using primary modulation: Theory and preliminary results." IEEE transactions on medical imaging, vol. 25, No. 12 (2006): 1573-1587.

* cited by examiner

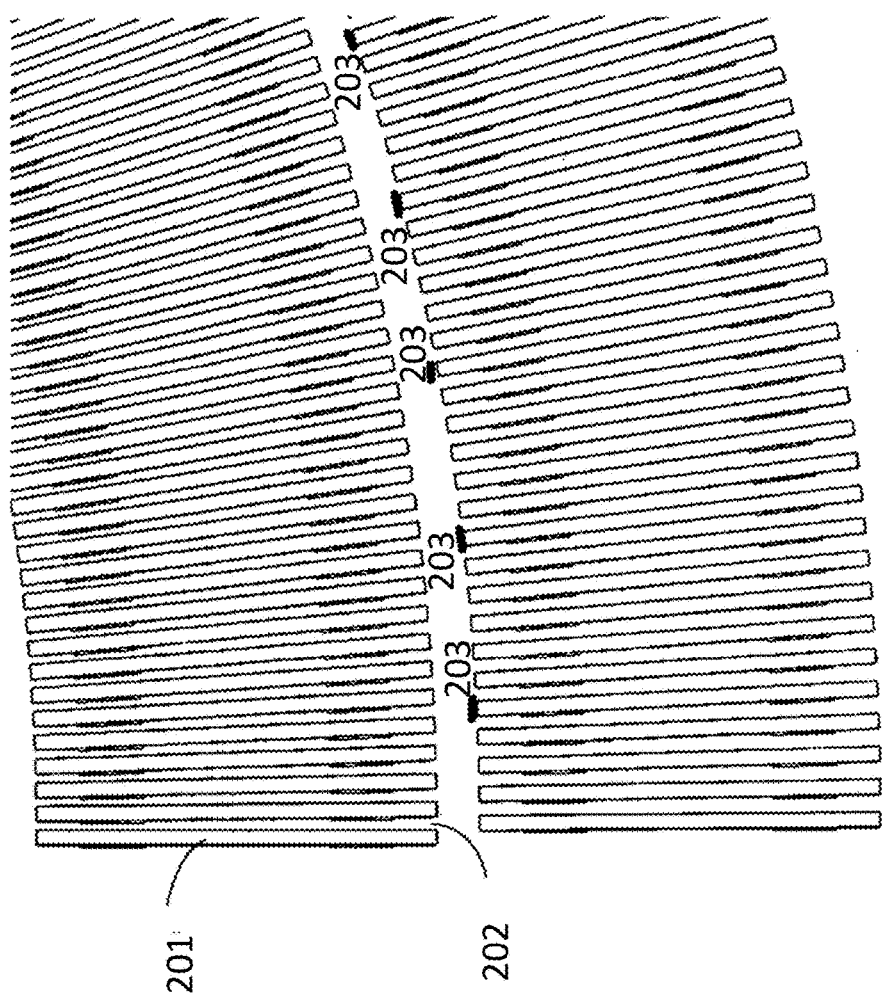

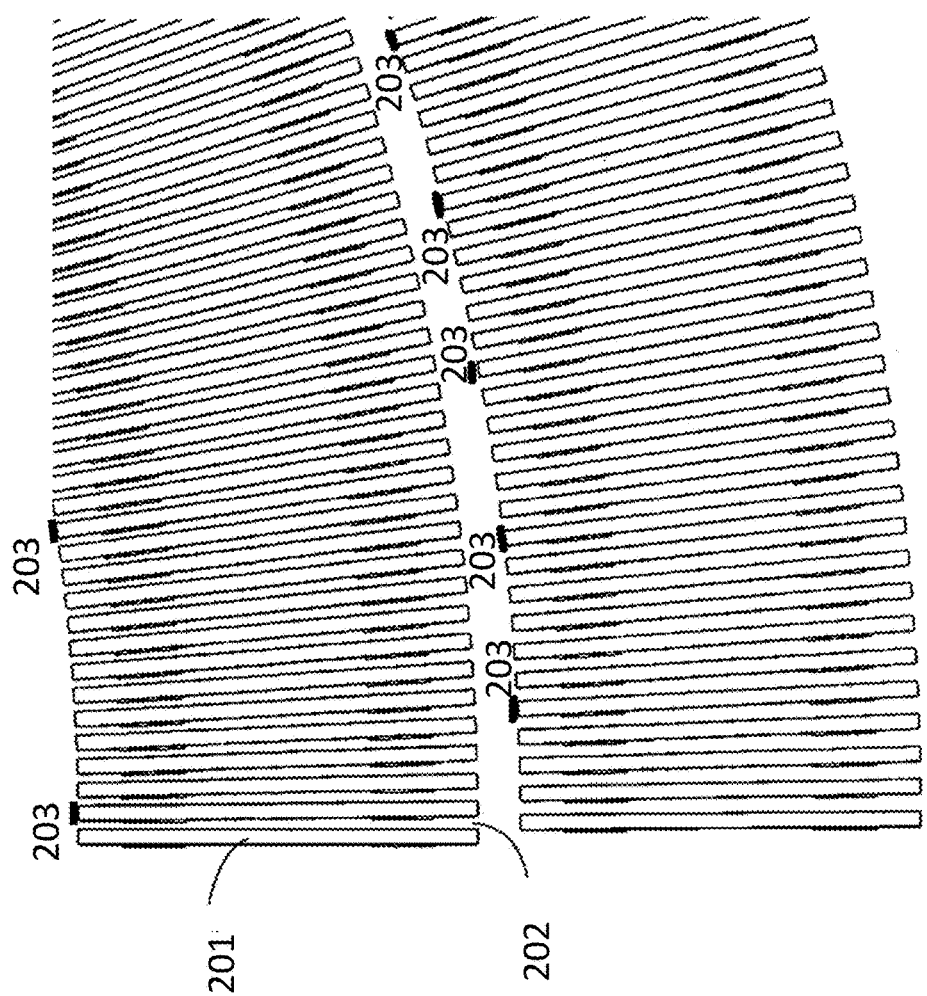

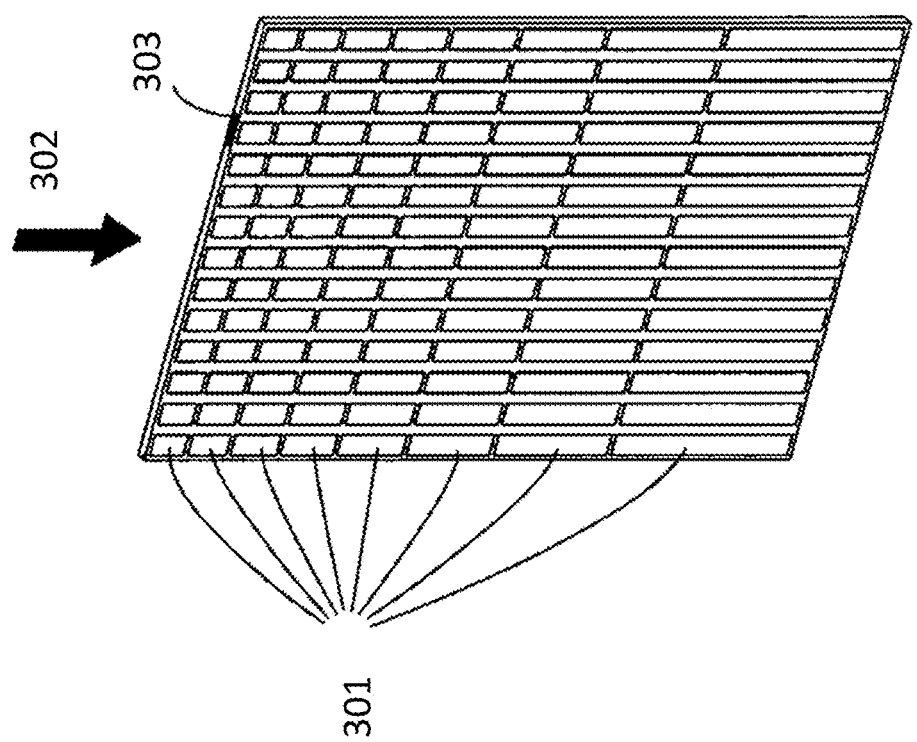

SCATTER ESTIMATION AND/OR CORRECTION IN X-RAY IMAGING

TECHNICAL FIELD

The here presented technology generally relates to scatter estimation and/or correction in x-ray imaging, and more particularly to method(s) and device(s) to estimate and/or compensate for object scatter and/or internal (detector crosstalk) scatter in a multi-level stacked (direct conversion) photon counting x-ray detector.

BACKGROUND

X-ray imaging is a common procedure, in medical imaging the energy range for the x-rays is typically 10 keV to 200 keV, in non-destructive testing or security screening the energy may be higher. In this range the x-rays reacts with matter mainly through Compton effect and Photoelectric effect. In the first case only a part of the energy of the x-ray photon is passed on to the electron and the x-ray continues with decreased energy after this scattering event. In the latter case all the energy is passed to the electron and the x-ray is completely absorbed.

A challenge for x-ray imaging detectors is to extract maximum information from the detected x-rays to provide input to an image of an object where the object is depicted in terms of density, composition and structure. It is still common to use film-screen as detector but mostly the detectors today provide a digital image.

The detector needs to convert the incident x-rays into electrons, this typically take place through Photo-effect or through Compton interaction and the resulting electron are usually creating secondary visible light until its energy is lost and this light is in turn detected by a photo-sensitive material. There are also detectors, less common, which are based on semiconductors such as amorphous Selenium or Silicon and in this case the electrons created by the x-ray is creating electric charge in terms of electrons and hole-pairs which are collected through an applied electric field with enough strength.

In computed tomography (CT) it is preferable to have a large detector; the detector size in the direction of the rotation determines the field-of-view and a large z-coverage tangential to the direction of the rotation (length in the scan direction) is essential for both fast full body acquisition in spiral mode scanning and the capability of covering entire organs in a single rotation. Imaging a large object (like a human patient) with a large detector however results in large scatter-to-primary ratios which degrades image quality by reducing contrast and introducing artifacts. Several different methods exist for combating the deteriorating effects of scatter. In essence, all fall in one of the following two categories:

A. Eliminating object scatter from reaching the detector
B. Estimating the scatter distribution and correcting for it either by means of simple subtraction of the spatial scatter profile or some type of de-convolution.

Methods for eliminating scatter to reach the detector include air gaps and anti-scatter grids and the use of the latter techniques come at the cost of absorbing primary x-rays as well thus reducing the dose efficiency of the system.

Methods for estimating the spatial distribution of the object scatter include:

A. Beam stop methods (U.S. Pat. No. 6,618,466 B1) where small and highly absorbing objects (such as lead beads) are placed in the beam path between the x-ray source and the objects. The corresponding locations on the detector are thus blind to primary radiation and the detector elements only measure the scattered radiation at that point. Since the scatter profile is spatially slowly varying (low frequency components) the beam stops can be rather sparsely distributed and still yield an adequate measure of the scatter profile.

B. Monte Carlo, or semi-analytical simulation models, whereby either the outline of the object, or a reconstructed slice, is used to estimate the object scatter profile on the detector. The second method is a key step in current iterative reconstruction methods.

The main purpose of scatter rejection and compensation methods to date has been to remove image artifacts and increase image contrast. With the advent of spectral photon counting computed tomography, where each photon is counted individually and assigned to an energy bin dependent on the amount of energy it deposits in the detector, accurate knowledge of the amount of scatter in each projection has become even more important. The reason is that one of the promises of spectral photon counting CT is to be able to perform material basis decomposition in the projection domain and thus achieve quantitative CT. Material basis decomposition is performed by solving a maximum likelihood problem. The counts in the bins are used to obtain a set of line integrals of the material basis coefficients in each projection and if the counts include an unknown number of events from scattered radiation, the line integral estimates will be biased which, in the reconstructed image, translates to biased material basis coefficients. The maximum likelihood method for obtaining the line integral estimates from the bin counts is well described by Roessl and Proksa in "K-edge imaging in x-ray computed tomography using multi-bin photon counting detectors", Physics in Medicine and Biology, vol 52, pp. 4679-96, 2007.

In conclusion, accurate scatter estimates are necessary to unlock the benefits of spectral photon-counting computed tomography.

U.S. Pat. No. 8,183,535 B2 describes a photon-counting energy sensitive detector intended for use mainly in computed tomography. A main feature of is the use of at least two levels of silicon diodes mounted in an edge-on geometry. This is illustrated in FIGS. 10a, 10b, 10c, 10d and 11 of U.S. Pat. No. 8,183,535 B2. A second feature is to use thin tungsten (or any other suitable x-ray absorber) lamella on the backside of each diode. The tungsten lamella serves as a built-in anti-scatter grid, reducing both object scatter and the secondary events which are generated from Compton interaction in the detector material due to the low atomic number of silicon.

It is of general interest to obtain improved image quality by providing efficient scatter estimation and/or correction for this and other types of photon-counting x-ray detectors.

SUMMARY

It is an object to provide a method and device as well as a corresponding computer program for estimating object scatter in a photon-counting x-ray detector.

It is also an object to provide a method and device as well as a corresponding computer program for estimating internal scatter of a photon-counting x-ray detector.

Another object is to provide methods and devices for adjusting measured counts in a layered photon-counting x-ray detector.

Yet another object is to provide methods and devices for estimating the total amount and spatial profile of scattered radiation absorbed in a layered photon-counting x-ray detector.

Still another object is to provide methods and devices for x-ray tomographic imaging of an object while correcting for scatter.

According to a first aspect, there is provided a method for estimating object scatter in a photon-counting x-ray detector having at least two layers of detector diodes mounted in an edge-on geometry or at least two layers of diode segments of diodes segmented in the direction of the incoming x-rays,
characterized by estimating the object scatter contribution to the counts in a top layer of said at least two layers based on difference(s) in counts between the top layer and lower layer(s) under the assumption that object scatter has a slowly varying spatial distribution.

According to a second aspect, there is provided a method for estimating internal scatter of a photon-counting x-ray detector having at least two layers of detector diodes mounted in an edge-on geometry or at least two layers of diode segments of diodes segmented in the direction of the incoming x-rays,
characterized by estimating counts from reabsorption of photons that have Compton scattered inside the detector based on selectively blinding some detector elements from primary radiation by placing a highly attenuating beam stop on top of the detector elements, in lower layer(s) or in both top layer and lower layer(s), and measuring the counts in those detector elements.

According to a third aspect, there is provided a method for adjusting measured counts in a layered photon-counting x-ray detector having at least two layers of detector diodes mounted in an edge-on geometry or at least two layers of diode segments of diodes segmented in the direction of the incoming x-rays,
characterized by adjusting the measured counts at least partly based on the object scatter estimated according to the method of the first aspect, to thereby obtain unbiased estimates of the counts due to primary x-ray interactions.

According to a fourth aspect, there is provided a method for adjusting measured counts in a layered photon-counting x-ray detector having at least two layers of detector diodes mounted in an edge-on geometry or at least two layers of diode segments of diodes segmented in the direction of the incoming x-rays,
characterized by adjusting the measured counts at least partly based on the internal scatter estimated according to the method of the second aspect, to thereby obtain unbiased estimates of the counts due to primary x-ray interactions.

According to a fifth aspect, there is provided a method for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays,
characterized by performing the estimation at least partly based on the object scatter estimated according to the method of the first aspect.

According to a sixth aspect, there is provided a method for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays,
characterized by performing the estimation at least partly based on the internal scatter estimated according to the method of the second aspect.

According to a seventh aspect, there is provided a method for x-ray tomographic imaging of an object while correcting for scatter, wherein said method comprises:
providing a source of x-ray radiation and detector comprising two layers of direct conversion semiconductor diodes pointing back to the source, wherein a spacing between individual diodes is provided in both a top and bottom layer that corresponds to the diode width, and a displacement of the bottom layer in the rotational direction such that primary x-rays missing the top layer diodes pass unattenuated to the lower level diodes;
moving the source and detector around the object obtaining projection x-ray images at different rotation angles;
detecting radiation from the source by the detector; and
estimating, for each rotation angle, the distribution of object scatter on the top layer of the detector based on the fact that the lower layer of the detector is shielded from object scatter by virtue of the top layer functioning like an anti-scatter grid with very high aspect ratio.

According to an eighth aspect, there is provided a method for x-ray tomographic imaging of an object while correcting for scatter, wherein said method comprises:
providing a source of x-ray radiation and detector comprising two layers of direct conversion semiconductor diodes pointing back to the source, wherein a spacing between individual diodes is provided in both a top and bottom layer that corresponds to the diode width, and a displacement of the bottom layer in the rotational direction such that primary x-rays missing the top layer diodes pass unattenuated to the lower level diodes;
providing beam stops, covering less than 50% of all detector channels and distributed across the entire detector, in the bottom layer or both the top and bottom layers, making them essentially blind to primary unscattered x-rays;
moving the source and detector around the object obtaining projection x-ray images at different rotation angles;
detecting radiation from the source by the detector;
estimating, for each rotation angle, the distribution of the sum of object and internal scatter of each layer by fitting a parametric surface to the counts of the detector elements with beam stops mounted on top of them; and
subtracting the estimated sum of object and internal scatter from each detector element not covered with beam stops, thus obtaining an estimate of the scatter free signal of each detector element not covered with beam stops.

According to a ninth aspect, there is provided a device for estimating object scatter in a photon-counting x-ray detector having at least two layers of detector diodes mounted in an edge-on geometry or at least two layers of diode segments of diodes segmented in the direction of the incoming x-rays,
wherein said device is configured to estimate the object scatter contribution to the counts in a top layer of said at least two layers based on difference(s) in counts between the top layer and lower layer(s) under the assumption that object scatter has a slowly varying spatial distribution.

According to a tenth aspect, there is provided a device for estimating internal scatter of a photon-counting x-ray detector having at least two layers of detector diodes mounted in an edge-on geometry or at least two layers of diode segments of diodes segmented in the direction of the incoming x-rays, wherein said device is configured to estimate counts from reabsorption of photons that have Compton scattered inside the detector based on measuring counts in detector elements having a highly attenuating beam stop placed on top of the detector elements, in lower layer(s) or in both top layer and lower layer(s).

According to an eleventh aspect, there is provided a device for adjusting measured counts in a layered photon-counting x-ray detector having at least two layers of detector diodes mounted in an edge-on geometry or at least two layers of diode segments of diodes segmented in the direction of the incoming x-rays, wherein said device comprises a device of the ninth aspect.

According to a twelfth aspect, there is provided a device for adjusting measured counts in a layered photon-counting x-ray detector having at least two layers of detector diodes mounted in an edge-on geometry or at least two layers of diode segments of diodes segmented in the direction of the incoming x-rays, wherein said device comprises a device of the tenth aspect.

According to a thirteenth aspect, there is provided a device for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays, wherein said device comprises a device of the ninth aspect.

According to a fourteenth aspect, there is provided a device for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays, wherein said device comprises a device of the tenth aspect.

According to a fifteenth aspect, there is provided a device for x-ray tomographic imaging of an object while correcting for scatter, wherein said device comprises:
  a source of x-ray radiation and a detector comprising two layers of direct conversion semiconductor diodes pointing back to the source,
  wherein there is a spacing between individual diodes in both a top and bottom layer that corresponds to the diode width, and a displacement of the bottom layer in the rotational direction such that primary x-rays missing the top layer diodes pass unattenuated to the lower level diodes,
  wherein the source and detector are arranged to be moved around the object obtaining projection x-ray images at different rotation angles, controlled by a movement controller; and
  an estimator, connected to the detector and arranged for obtaining measurement data from the detector, or being an integrated part of the detector, wherein the estimator is configured for estimating, for each rotation angle, the distribution of object scatter on the top layer of the detector, using the fact that the lower layer of the detector is shielded from object scatter by virtue of the top layer functioning like an anti-scatter grid with very high aspect ratio.

According to a sixteenth aspect, there is provided a device for x-ray tomographic imaging of an object while correcting for scatter, wherein said device comprises:
  a source of x-ray radiation and detector comprising two layers of direct conversion semiconductor diodes pointing back to the source,
  wherein there is a spacing between individual diodes in both a top and bottom layer that corresponds to the diode width, and a displacement of the bottom layer in the rotational direction such that primary x-rays missing the top layer diodes pass unattenuated to the lower level diodes,
  wherein beam stops are provided, covering less than 50% of all detector channels and distributed across the entire detector, in the bottom layer or both the top and bottom layers, making them essentially blind to primary unscattered x-rays;
  wherein the source and detector are arranged to be moved around the object obtaining projection x-ray images at different rotation angles, controlled by a movement controller; and
  an estimator, connected to the detector and arranged for obtaining measurement data from the detector, or being an integrated part of the detector, wherein the estimator is configured for estimating, for each rotation angle, the distribution of the sum of object and internal scatter of each layer by fitting a parametric surface to the counts of the detector elements with beam stops mounted on top of them, and the estimated sum of object and internal scatter is subtracted from each detector element not covered with beam stops, thus obtaining an estimate of the scatter free signal of each detector element not covered with beam stops.

According to a seventeenth aspect, there is provided a computer program for estimating, when executed by a processor, object scatter in a photon-counting x-ray detector having at least two layers of detector diodes mounted in an edge-on geometry or at least two layers of diode segments of diodes segmented in the direction of the incoming x-rays,
  wherein said computer program comprises instructions, which when executed by the processor, cause the processor to estimate the object scatter contribution to the counts in a top layer of said at least two layers based on difference(s) in counts between the top layer and lower layer(s) under the assumption that object scatter has a slowly varying spatial distribution.

According to an eighteenth aspect, there is provided a computer program for estimating, when executed by a processor, internal scatter of a photon-counting x-ray detector having at least two layers of detector diodes mounted in an edge-on geometry or at least two layers of diode segments of diodes segmented in the direction of the incoming x-rays,
  wherein said computer program comprises instructions, which when executed by the processor, cause the processor to estimate counts from reabsorption of photons that have Compton scattered inside the detector based on measurements of counts in detector elements having a highly attenuating beam stop placed on top of the detector elements, in lower layer(s) or in both top layer and lower layer(s).

According to a nineteenth aspect, there is provided a computer-program product comprising a computer-readable medium having stored thereon such a computer program.

A good understanding and knowledge of the scatter situation in x-ray detectors is of crucial importance for enabling improved image quality, artifact reduction and/or improved material basis decomposition.

Other aspects and advantages of the currently presented technology will be appreciated when reading the below description.

BRIEF DESCRIPTION OF DRAWINGS

The currently presented technology, together with further objects and advantages thereof, may best be understood by making reference to the following description taken together with the accompanying drawings, in which:

FIGS. 2A and 2B are side views of the detector layers where 201 is a silicon diode wafer, 202 is a spacing between top layer diodes where primary x-rays entering the bottom layer pass. 203 are the beam stops selectively blinding some detector elements of the lower layer of diodes and of both layers, respectively.

FIG. 3 is a schematic of a single silicon diode where 301 indicate electrodes for charge collection, 302 the direction of incoming photons and 303 a beam stop blinding all primary x-rays for one particular row of electrodes.

DETAILED DESCRIPTION

Figure 1:
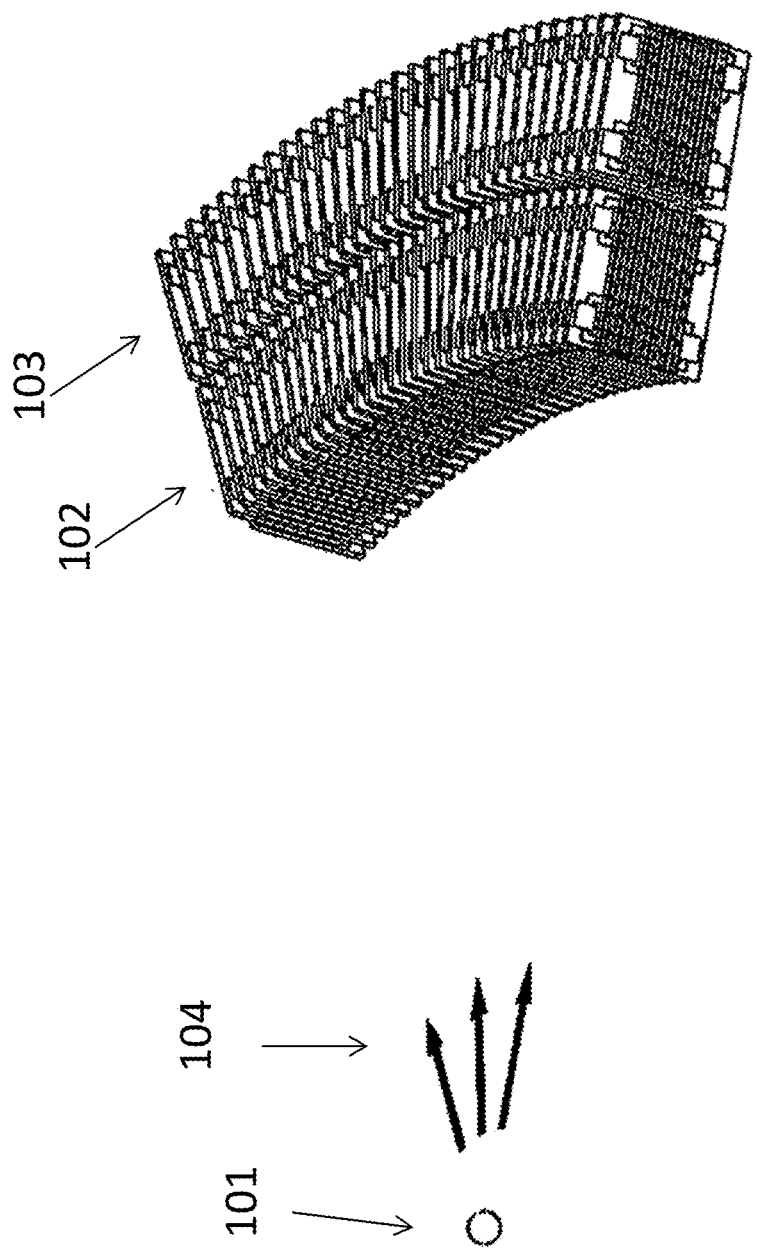
FIG. 1 is a schematic diagram illustrating an example of two layers of silicon diode wafers (102 is top layer, 103 is lower layer) pointing back to the x-ray source 101.

According to a first aspect, there is provided a method for estimating object scatter in a photon-counting x-ray detector having at least two layers of detector diodes mounted in an edge-on geometry or at least two layers of diode segments of diodes segmented in the direction of the incoming x-rays,
characterized by estimating the object scatter contribution to the counts in a top layer of said at least two layers based on difference(s) in counts between the top layer and lower layer(s) under the assumption that object scatter has a slowly varying spatial distribution.

According to a second aspect, there is provided a method for estimating internal scatter of a photon-counting x-ray detector having at least two layers of detector diodes mounted in an edge-on geometry or at least two layers of diode segments of diodes segmented in the direction of the incoming x-rays,
characterized by estimating counts from reabsorption of photons that have Compton scattered inside the detector based on selectively blinding some detector elements from primary radiation by placing a highly attenuating beam stop on top of the detector elements, in lower layer(s) or in both top layer and lower layer(s), and measuring the counts in those detector elements.

By way of example, the estimation may be performed for each of a number of projections during rotation of a gantry of a computed tomography system.

In a particular example, the x-ray detector is a direct conversion x-ray detector using a direct-converter material.

For example, the direct-converter material may be Silicon.

In another particular example, the top layer acts as an anti-scatter grid for the lower layer(s).

According to a third aspect, there is provided a method for adjusting measured counts in a layered photon-counting x-ray detector having at least two layers of detector diodes mounted in an edge-on geometry or at least two layers of diode segments of diodes segmented in the direction of the incoming x-rays,
characterized by adjusting the measured counts at least partly based on the object scatter estimated according to the method of the first aspect, to thereby obtain unbiased estimates of the counts due to primary x-ray interactions.

By way of example, the measured counts are adjusted based on the estimated object scatter and a constant $\gamma$, which relates internal detector scatter as a constant fraction $\gamma$ of the sum of the counts from primary x-ray interactions and object scatter in a local neighborhood.

According to a fourth aspect, there is provided a method for adjusting measured counts in a layered photon-counting x-ray detector having at least two layers of detector diodes mounted in an edge-on geometry or at least two layers of diode segments of diodes segmented in the direction of the incoming x-rays,
characterized by adjusting the measured counts at least partly based on the internal scatter estimated according to the method of the second aspect, to thereby obtain unbiased estimates of the counts due to primary x-ray interactions.

According to a fifth aspect, there is provided a method for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays,
characterized by performing the estimation at least partly based on the object scatter estimated according to the method of the first aspect.

According to a sixth aspect, there is provided a method for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays,
characterized by performing the estimation at least partly based on the internal scatter estimated according to the method of the second aspect.

In an illustrative example of the current presented technology it is desirable to provide an improved image quality for a system with at least two levels of (silicon) diodes mounted in an edge on geometry of a same kind as described in U.S. Pat. No. 8,183,535 B2 by estimating the total amount and spatial profile of the scattered radiation absorbed in the detector in each of a number of projections (image acquisition) during the gantry rotation. In particular it is desirable to be able to measure the scatter contribution in the detector without resorting to estimates based on computer simulations. It is also desirable to be able to measure the object scatter and the internal detector scatter separately.

Placing the silicon detector diodes in two or more layers in a system with at least two levels of silicon diodes mounted in an edge on geometry of a same kind as described in U.S. Pat. No. 8,183,535 B2 is useful to obtain full x-ray coverage and avoid leaving any blind spots. The reason is that the ASICs and other components mounted on the diode wafer (which is of approximate thickness 0.5 mm) protrude a few tenths of a millimeter and thus make stacking in one layer geometrically impossible. In addition, the stacking enables efficient cooling schemes of the detector diodes since air can be blown through the layers.

The arrangement with two layers of detector diodes oriented back towards the source (FIG. 1) also brings another benefit; the top layer in essence acts as an anti-scatter grid with a very high grid ratio for the lower level. Indeed, computer based Monte Carlo simulations have shown that in a two-layer version, the lower layer is almost entirely free of object scatter. If the diodes of the top layer are slightly misaligned they shadow the lower level diodes which result in decrease in primary counts compared to the top layer. This effect can also come from the anti-scatter plate, e.g. a tungsten plate, of the first layer shadowing the lower level.

If the diode is electronically segmented in the direction of the incoming x-rays, 301, the lower part of the diode is shielded from object scatter by the upper part. Therefore the lowest segments will measure less object scatter than the upper parts and this difference can be used in the same way as with multiple layers.

The proposed technology thus generally relates to a photon-counting x-ray detector having at least two layers of detector diodes mounted in an edge-on geometry or at least two layers of segments of diodes segmented in the direction of the incoming x-rays. The latter case refers to a detector based on segmented diodes with at least two levels of segments.

The top layer is the layer closest to the x-ray source and the lower layer(s) are the one(s) further away from the x-ray source.

Alternatively, the x-ray detector may be regarded as a multi-level detector where the levels may correspond to layers of detector diodes or levels of diode segments.

It is well established that the object scatter profile is slowly varying, i.e. its spatial frequency components are concentrated towards lower values (Zhu, Bennett and Fahrig, "Scatter correction method for x-ray CT using primary modulation: theory and preliminary results" in IEEE Transactions of Medical Imaging, vol 25, pp. 1573-1587, 2006).

According to one aspect of the current presented technology, there is provided a method for estimating the object scatter contribution on the top layer of the detector by utilization of its low spatial frequency characteristics and the difference(s) in counts in the first and lower layer(s).

According to another aspect, there is provided a method for estimating the internal scatter profile from Compton interactions inside the detector. This is achieved by selectively blinding some detector elements from primary radiation by placing a highly attenuating beam stop on top of it, i.e. after the object. This is different from other beam stop methods proposed in literature, such as U.S. Pat. No. 6,618,466 B1, where the beam stop is placed between the source and the object for the purpose of estimating scatter emanating from the object.

According to yet another aspect, there is provided a computer program and corresponding computer program product for implementation of the object scatter spatial profile estimation method and the corresponding adjustment of the counts in the bins. Typical adjustments are to subtract the scatter profile counts, or to include the scatter estimates of each projection in the material basis decomposition problem. See for instance Equation 2 in Bornefalk, Persson and Danielsson, "Allowable forward model misspecification for accurate basis decomposition in a silicon detector based spectral CT" in IEEE Transactions of Medical Imaging vol. 34, pp. 788-795, 2015. Regardless of adjustment method selected, the goal is to get the best possible estimate of the number of primary x-ray interactions in each projection since this will avoid bias and artifacts in the final reconstructed image.

By way of example, the invention offers at least one of the following advantages:
A. Artifact reduction in reconstructed CT images
B. Non-biased solutions to the material basis decomposition method which enables quantitative CT U.S. Pat. No. 8,183,535 B2 "Silicon detector assembly for X-ray imaging" describes a photon-counting energy sensitive detector intended for use mainly in computed tomography. Silicon diodes are mounted in an edge on geometry. This is illustrated in FIG. 1 where 101 is the x-ray source and 104 the direction of the x-rays.

In FIG. 3 it is seen how the x-rays, due to the edge on geometry, traverse relatively large distances, e.g. several centimeters of silicon which results in a high detection efficiency. In FIG. 3, 302 is the direction of the primary x-rays and 301 indicate how the generated charge clouds are collected by several electrodes (detector elements) distributed along the path of interaction.

A single diode (sensor) in essence acts a layered detector by itself. By applying a reverse bias voltage over the diode, the charge collection electrodes denoted 301 shape the electric field across the diode such that x-ray interactions generating charge only generate a pulse in the channel connected to the electrode 301 closest to the actual x-ray conversion.

In x-ray computed tomography scattered radiation is a problem that results in image artifacts. It also makes the method of material basis decomposition more difficult since the scatter-to-primary ratio for each projection (each measurement in a detector element) must be known to within a few percentage units. Reference can be made to Bornefalk, Persson and Danielsson, "Allowable forward model misspecification for accurate basis decomposition in a silicon detector based spectral CT" in IEEE Transactions of Medical Imaging vol. 34, pp. 788-795, 2015. If the number of counts due to scattered radiation depositing energy in the detector is not well-enough known, the result will be biased estimate of the line integrals of the basis function coefficients which will in turn makes quantitative CT impossible. Quantitative CT allows accurate measurements of iodine contrast agent concentration from the reconstructed image and also allows the radiologist to make other quantitative measurement in the image, such as the density of a tumor or the composition of a cyst. In addition, material basis decomposition is essential for removing beam hardening artifacts.

Scatter counts typically have two sources; object scatter from the object being imaged and events that have scattered inside the detector. For low atomic number direct converter materials like silicon, the latter source is a larger problem than for converter materials that have high photoelectric cross section in the diagnostic imaging range. Simulations have shown that the scatter-to-primary ratio attributable to internal scatter, i.e. reabsorption of Compton-scattered photons, is approximately 8% for the system described in U.S. Pat. No. 8,183,535 B2. Reference can be made to Bornefalk and Danielsson, "Photon-counting spectral computed tomography using silicon strip detectors: a feasibility study", Physics in Medicine and Biology, vol. 55, pp. 1999-2022, 2010.

The scatter-to-primary ratio of events falling onto the top layer of the detector can be several hundreds of percent if the object being imaged is large. For this reason thin anti-scatter elements, such as tungsten lamellae, of approximate thickness 50 micrometers (although other thicknesses may also work, e.g. in the range of 30-150 micrometers), may be mounted on the backside of each diode. This results in efficient, but not perfect, scatter rejection in the top layer, without being as detrimental to the geometric detection efficiency as traditional anti-scatter grids that remove up to 30% of primary x-rays with a correspond loss of dose efficiency. The lower level of diodes are shielded from object scatter in two ways; the first is the anti-scatter elements such as tungsten lamellae of the lower level diodes and the second is anti-scatter elements such as the tungsten lamellae and the diodes themselves in the top layer. Together they serve as an anti-scatter grid with very high aspect ratio. This is seen in FIG. 2. Computer simulations have shown that the de facto anti scatter grid that the top layer constitutes for the lower level is very efficient at removing object scatter; the registered counts in the lower level diodes are virtually free of counts emanating from scattered events in the object. The difference in counts in the top and bottom layers, together with the fact that object scatter has a slowly varying spatial distribution, can be used to estimate the object scatter contribution to the counts in the top layer.

Additionally, there are counts from reabsorption of photons that have Compton scattered inside the detector. In the lower layer, this will to a close approximation be the only scatter contribution. By selective blinding a small fraction of detector elements with a small beam stop (203, 303), either only in the lower layer or in both, the counts in those detector elements will be the result of scatter alone, i.e. no interactions from primary, undeflected, x-rays will have contributed to the counts.

Below two non-limiting example embodiments of methods will be described showing how the above insights can be used to estimate the spatial profile of the total amount of scatter absorbed in the detector, as well as object scatter and/or internal scatter. It is also shown how the primary counts can be estimated, both with and without the use of beam stops.

Consider one data measurement during the CT image acquisition, i.e. one complete readout of all detector elements at a certain rotation angle of the gantry. The diodes are indexed with j ranging from 1 to the number of diodes in each layer of the detector, $N_j$. A diode thickness of 0.5 mm indicate a center-to-center distance of the diodes in each layer of 1 mm. With an 800 mm wide detector in the rotational direction this indicates a value of $N_j=800$. Let k be the index of detector elements on each diode. In the example of FIG. 3 all segments 301 together constitute one detector element, as they all see the same ray from the source (302). k ranges from 1 to $N_k$ where $N_k$ is in the order of 50.

Finally let the total counts be denoted by c, the counts from primary radiation p, the counts from object scatter os and the count from internal detector scatter is.

Estimating Scatter and Primaries without Use of Beam Stops

The counts in a detector element k of a detector diode j in the top layer not covered by a beam stop can be written as:

$$c_{jk}^{top} = p_{jk}^{top} + os_{jk}^{top} + is_{jk}^{top} \quad (1)$$

and correspondingly in the lower layer:

$$c_{jk}^{lower} = p_{jk}^{lower} + is_{jk}^{lower}. \quad (2)$$

We now describe a first method of how $p_{jk}^{top}$ and $p_{jk}^{lower}$ can be estimated (yielding $\hat{p}_{jk}^{top}$ and $\hat{p}_{jk}^{lower}$), without the use of beam stops. Throughout this derivation, estimated parameter values are indicated with "hat", ^. Note that only $p_{jk}^{top}$ and $p_{jk}^{lower}$ are observable.

The first insight is that counts from primary x-rays exhibit high spatial frequency behavior, i.e. large differences $|p_{jk}^{top} - p_{lm}^{lower}|$ can be expected to be observed even for small detector element displacements $\sqrt{(l-m)^2-(m-k)^2}$. This is in contrast to the Compton scatter component $os_{jk}^{top}$ which is slowly varying, i.e. $|os_{jk}^{top} - os_{lm}^{top}| \approx 0$ for $\sqrt{(l-m)^2-(m-k)^2} < \epsilon$ where $\epsilon$ is a small value (in the order of 10).

The second insight used is that internal scatter inside the detector is also slowly varying and that its magnitude can either be proportional to the average number of events from object scatter and primary x-rays in a local neighborhood of that layer, i.e. the expected value of the internal scatter can be written as:

$$E(is_{jk}^{top}) = \frac{\gamma}{|\Omega|} \sum_{l,m \in \Omega} (p_{lm}^{top} + os_{lm}^{top}), \quad (3a)$$

$$E(is_{jk}^{lower}) = \frac{\gamma}{|\Omega|} \sum_{l,m \in \Omega} (p_{lm}^{lower}) \quad (3b)$$

where the summation is carried out over some local neighborhood $\Omega$, for instance one given by $\sqrt{(l-m)^2-(m-k)^2} < L$ where L is related to the typical mean free path of scattered photons. $|\Omega|$ the number of elements in the set $\Omega$ and $\gamma$ is a kVp-dependent constant in the vicinity of 8% according to previous work. Reference can be made to Bornefalk and Danielsson, "Photon-counting spectral computed tomography using silicon strip detectors: a feasibility study", Physics in Medicine and Biology, vol. 55, pp. 1999-2022, 2010.

If Eq. 2 is subtracted from Eq. 1 after scaling one gets:

$$d(j,k) = c_{jk}^{top} - \alpha_{jk} \times c_{jk}^{lower} = p_{jk}^{top} + os_{jk}^{top} + is_{jk}^{top} - \alpha_{jk}p_{jk}^{lower} - \alpha_{jk}is_{jk}^{lower}\alpha_{jk}^{lower}. \quad (4)$$

The scale factor $\alpha_{jk}$, typically $1 \leq \alpha_{jk} < 1.5$ captures the degree to which the lower layer diodes count less primary photons due to possible shadowing by the top layer. The exact value of $\alpha_{jk}$ for each position (each index combination) is determined in a calibration procedure when the detector is assembled and it will be dependent of the x-ray tube acceleration voltage.

Note that indices j refer to the number of the diode and k to the detector elements on each diode. Thus the top and bottom layer index j do not correspond to the exact same spatial location, there is an offset of one diode wafer thickness (0.5 mm).

The difference d(j,k) of Eq. 4 will contain high frequency components from the difference between primary events $p_{jk}^{top} - \alpha p_{jk}^{lower}$ and mainly low frequency contributions from the scatter. The expected value of the weighted primary signal difference is:

$$E(p_{jk}^{top} - \alpha_{jk}p_{jk}^{lower}) \approx 0. \quad (5)$$

If the difference signal d(j,k) is convolved with a suitable low pass filter h(j,k), for example a Gaussian filter with support over $\Omega$, the result, with the use of Eqs. 3a and 3b and Eq 5, is:

$$h(j,k) * d(j,k) = h(j,k) * (p_{jk}^{top} - \alpha_{jk}p_{jk}^{lower}) + \quad (6)$$

$$h(j,k) * \left( os_{jk}^{top} + \frac{\gamma}{|\Omega|} \sum_{l,m \in \Omega} (p_{lm}^{top} + os_{lm}^{top} - \alpha_{jk}p_{lm}^{lower}) \right) =$$

$$h(j,k) * \left( os_{jk}^{top} + \gamma \overline{os_{jk}^{top}} \right)$$

where $\overline{os_{jk}^{top}}$ is the average value of the object scatter over $\Omega$ centered at j,k.

Since $os_{jk}^{top}$ contains only low frequencies, it is essentially left unaltered by both the convolution and the averaging and we can therefore estimate it by:

$$\widehat{os}_{jk}^{top} = \frac{d(j,k) * h(j,k)}{(1+\gamma)}. \tag{7}$$

A second possibility would be to fit the difference signal d(j,k) of Eq. 4 to a parametric surface over the entire detector plane. For the particular case of a polynomial parametric surface of dimensionality N the object scatter for all positions j,k of detector would be estimated by:

$$\widehat{os}_{jk}^{top} = \sum_{n=0}^{N} \alpha_n j^s k^t / (1+\gamma), s+t \le n \text{(integers)} \tag{8}$$

where the parameter set can be determined either by maximum likelihood estimation, taking the Poisson nature of the counts into consideration, or a least squares solution:

$$\{\alpha_n\} = \text{argmin}_{\{\beta_n\}} \Sigma_{j,k} (d(j,k) - \Sigma_{n=0}^{N} \beta_n j^s k^t)^2, s+t \le n. \tag{9}$$

Once the object scatter of the top layer is estimated, the primary signals in the top and bottom layers can be determined as:

$$\hat{p}_{jk}^{top} = \frac{c_{jk}^{top} - \widehat{os}_{jk}^{top}}{(1+\gamma)} \tag{10}$$

$$\hat{p}_{jk}^{lower} = \frac{c_{jk}^{lower}}{(1+\gamma)} \tag{11}$$

Eq. 10 and 11 do not take advantage of the fact that internal scatter is also slowly varying. An alternative method that includes this is to low pass filter the counts and then subtract the appropriate fraction of the low passed version instead of using division. With $h(j,k)*c_{jk}^{lower}$ being the low pass filtered version of counts in detector element j,k of the lower layer, a better estimate of the primaries would be:

$$\hat{p}_{jk}^{lower} = c_{jk}^{lower} - \frac{\gamma}{1+\gamma} h(j,k) * c_{jk}^{lower}. \tag{12}$$

For the top layer the corresponding estimate would be (where the bar indicates low pass filtration):

$$\hat{p}_{jk}^{top} = c_{jk}^{top} - \widehat{os}_{jk}^{top} - \frac{\gamma}{1+\gamma} h(j,k) * (c_{jk}^{top} - \widehat{os}_{jk}^{top}) \tag{13}$$

The above derivation has been carried out in photon counting mode, i.e. where all events are collected in the same bin. It is an obvious extension of the method to treat the energy bins separately.

Estimating Scatter and Primaries with Beam Stops in Both Layers

For a selected combination of indices j and k that have a beam stop mounted (203, 303) (indices denoted with primes, i.e. the set is a subset of {j,k}), the relationships will be the following due to the absence of primary events:

$$c_{j',k'}^{top} = os_{j',k'}^{top} + is_{j',k'}^{top} \tag{14}$$

and correspondingly in the lower layer where there are no object scattered events:

$$c_{j',k'}^{lower} = is_{j',k'}^{lower} \tag{15}$$

To minimize the loss of primary radiation (which degrades dose efficiency) the indices j', k' will be sparsely distributed. For this reason a convolution method is not suitable. Instead a parametric surface is fitted to the measurements, in the below example a polynomial. For the top layer this means that it is the sum of the object scatter and internal scatter that is estimated:

$$\left(\widehat{os}_{jk}^{top} + \widehat{is}_{jk}^{top}\right) = \sum_{n=0}^{N} \alpha_n j^s k^t, s+t \le n \text{(integers)} \tag{16}$$

where the parameters are determined either by maximum likelihood estimation or a least squares method solved over the blinded detector elements:

$$\{\alpha_n\} = \text{argmin}_{\{\beta_n\}} \Sigma_{j',k'} (c_{j',k'}^{top} - \Sigma_{n=0}^{N} \beta_n j^s k^t)^2. \tag{17}$$

From this, the primary counts in the top layer are estimated using Eq. 1 and Eq. 16 as:

$$\hat{p}_{jk}^{top} = c_{jk}^{top} - \left(\widehat{os}_{jk}^{top} + \widehat{is}_{jk}^{top}\right). \tag{18}$$

For the lower level the same method applies, with:

$$\widehat{is}_{jk}^{lower} = \Sigma_{n=0}^{N} \alpha_n j^s k^t, s+t \le n, \text{ where} \tag{19}$$

$$\{\alpha_n\} = \text{argmin}_{\{\beta_n\}} \Sigma_{j',k'} (c_{j',k'}^{lower} - \Sigma_{n=0}^{N} \beta_n j^s k^t)^2. \tag{20}$$

$$\hat{p}_{jk}^{lower} = c_{jk}^{lower} - \widehat{is}_{jk}^{lower}. \tag{21}$$

Estimating scatter and primaries with beam stops in only the lower layer is also possible to perform in an analogue manner.

In conclusion we have presented a method for adjusting the measured counts in a photon counting layered detector to obtain unbiased estimates of the primary counts. The method can be implemented with and without beam stops and the location of the beam stops differ from that previously presented in the literature, i.e. after the object and directly on top of the detector instead of between the object and the x-ray source. The reason is that previous use of beam stops in x-ray imaging has had the goal of estimating the object scatter profile on the detector and not the internal detector scatter.

In one preferred embodiment the geometric configuration of the diodes results in an efficient anti-scatter grid for the lower level diodes and this allows estimation of the total scatter profile making some plausible assumptions regarding the inherent detector scatter and the spatial frequency distribution of the object scatter.

The above method can be applied to detector geometries where more than two layers are applied, since all layers above any given layer will act as anti-scatter grid for that layer.

The above method can also be applied to detector geometries with only one layer of semiconductor diodes if the diodes are segmented in the direction of the incoming photons, 301. In such arrangements, the lower part of the diode is shielded from object scatter by the upper part. Therefore the lowest segments will measure less object scatter than the upper parts and this difference can be used in the same way as with multiple layers.

In another preferred embodiment, the use of distributed beam stops inside the detector module allow direct estimation of the total distribution of scattered radiation, making use of the low spatial frequencies of the sum of the object scatter and inherent scatter.

The derivation and illustration has been performed for a photon counting detector without energy resolving capabilities, but applies equally well to multibin systems where events (photon conversion in the diode) increment different counters depending on how much energy is being deposited.

Figure 4:
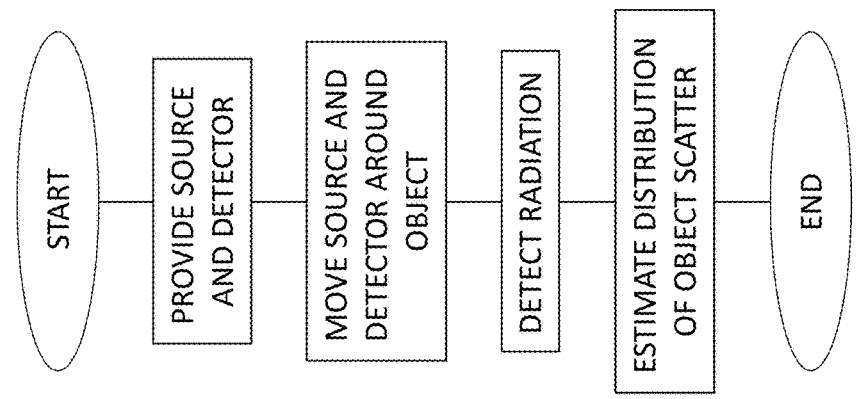
FIG. 4 is a flow diagram of steps of an embodiment of a method for x-ray tomographic imaging of an object.

In one particular embodiment, as illustrated in FIG. 4, a method for x-ray tomographic imaging of an object while correcting for scatter comprises providing a source of x-ray radiation and detector composed of two layers of direct conversion semiconductor diodes pointing back to the source. A spacing between individual diodes is provided in both the top and bottom layer that corresponds to the diode width, and a displacement of the bottom layer in the rotational direction such that primary x rays missing the top layer diodes pass unattenuated to the lower level diodes. The source and detector are moved around the object obtaining projection x-ray images at different rotation angles. Radiation from the source is detected by the detector. For each rotation angle the distribution of object scatter on the top layer of the detector is estimated using the fact that the lower layer of the detector is shielded from object scatter by virtue of the top layer functioning like an anti-scatter grid with very high aspect ratio.

The estimation comprises the following steps. For each detector element in the top row, the corresponding measurement from the bottom row, displaced one diode width in direction of rotation, is subtracted after weighting to adjust for any difference in mean detection efficiency, for instance stemming from shadowing. The low spatial frequency representation of the difference is determined by means of low pass filtering or fitting of a parametric surface. This low frequency representation is an estimate of the object scatter distribution across the entire top layer. The approximation that internal detector scatter is a constant fraction $\gamma$ of the sum of the counts from primary and object scatter in a local neighborhood is used to estimate the scatter free signal in each top layer detector element by either subtracting said estimated object scatter in that element and dividing the difference by $(1+\gamma)$ to compensate for internal detector scatter; or to subtract a fraction $1/(1+\gamma)$ of the difference between measured counts and said estimated object scatter after low pass filtration from the difference between measured counts and said estimated object scatter itself. The scatter free signal in each bottom layer detector element is estimated by dividing the measured signal with $(1+\gamma)$; or by subtracting a fraction $1/(1+\gamma)$ of the low passed measured signal in that detector element from the measured signal in that detector element itself.

In a preferred embodiment, the semiconductor diodes are made of silicon.

In a preferred embodiment, the number of semiconductor diode layers exceed two. In other words, the number of semiconductor diode layers is greater than two.

In a preferred embodiment, the layers constitute segments in the direction of the incoming x-rays in a diode.

Figure 5:
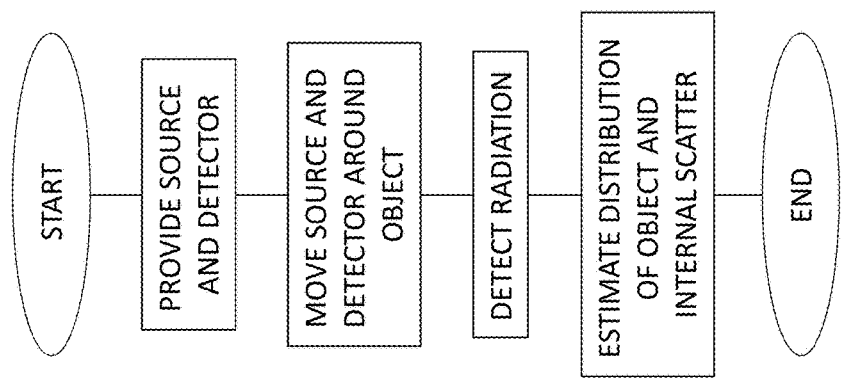
FIG. 5 is a flow diagram of steps of another embodiment of a method for x-ray tomographic imaging of an object.

In another particular embodiment, as illustrated in FIG. 5, a method for x-ray tomographic imaging of an object while correcting for scatter comprises providing of a source of x-ray radiation and detector composed of two layers of direct conversion semiconductor diodes pointing back to the source. A spacing between individual diodes is provided in both the top and bottom layer that corresponds to the diode width, and a displacement of the bottom layer in the rotational direction such that primary x rays missing the top layer diodes pass unattenuated to the lower level diodes. Beam stops are provided, covering less than 50% of all detector channels and distributed across the entire detector, both top and bottom layers, making them essentially blind to primary unscattered x-rays. The source and detector are moved around the object obtaining projection x-ray images at different rotation angles. Radiation from the source is detected by the detector. For each rotation angle the distribution of the sum of object and internal scatter of each layer is estimated by fitting a parametric surface to the counts of the detector elements with beam stops mounted on top of them. The estimated sum of object and internal scatter is subtracted from each detector element no covered with beam stops, thus obtaining an estimate of the scatter free signal of each detector element not covered with beam stops.

In a preferred embodiment, the semiconductor diodes are made of silicon.

In a preferred embodiment, the number of semiconductor diode layers exceed two. In other words, the number of semiconductor diode layers is greater than two.

Embodiments of a device for x-ray tomographic imaging of an object while correcting for scatter by the capabilities as described above may be based on a system with at least two levels of silicon diodes mounted in an edge on geometry of a same kind as being described in U.S. Pat. No. 8,183,535 B2.

The x-ray detector described in U.S. Pat. No. 8,183,535 specifically relates to a Silicon detector for x-ray imaging that is based on multiple semiconductor detector modules arranged together to form an overall detector area, where each semiconductor detector module comprises an x-ray sensor of crystalline Silicon oriented edge-on to incoming x-rays and connected to integrated circuitry for registration of x-rays interacting in the x-ray sensor through the photo-electric effect and through Compton scattering and for an incident x-ray energy between 40 keV and 250 keV to provide the spatial and energy information from these interactions to enable an image of an object. Further, anti-scatter modules are interfolded between at least a subset of the semiconductor detector modules to at least partly absorb Compton scattered x-rays.

As mentioned, semiconductor detector modules, each including an x-ray sensor, are tiled together to form a full detector of almost arbitrary size with almost perfect geometrical efficiency except for an anti-scatter grid which is integrated between at least some of the semiconductor detector modules. The x-ray sensors are attached to integrated circuits which use the information both from x-rays that Compton scatter in the sensors and from x-rays which reacts through photo-effect. This information is used to reconstruct the final image with optimum contrast for a certain imaging task. Preferably, the energy for each x-ray can be deduced with the combined information of the deposited energy in the semiconductor sensor and the depth of interaction for the x-ray. The anti-scatter grid which normally is made of a relatively heavy material not only cut Compton scattered x-rays from the object but also prevents Compton scattered x-rays in the semiconductor sensors to reach other sensors. These Compton scattered x-rays would otherwise mainly add to the noise.

Preferably, each anti-scatter module includes a foil of relatively heavy material to prevent most of the Compton scattered x-rays in a semiconductor detector module to reach an adjacent detector module.

Figure 8:
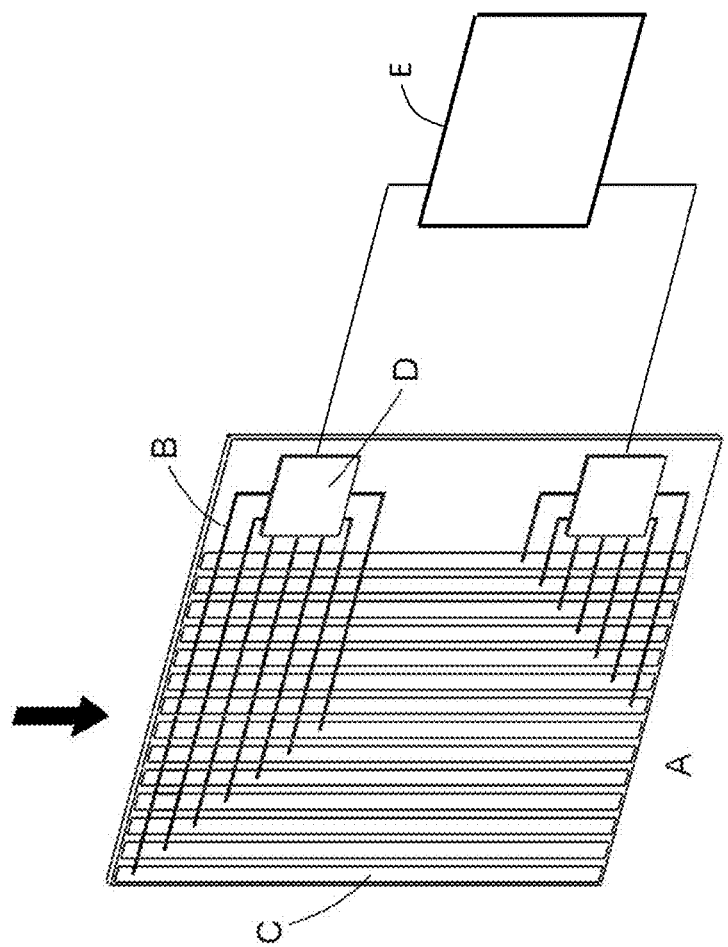
FIG. 8 is a schematic diagram illustrating an example of a semiconductor detector module implemented as a multi-chip module according to an exemplary embodiment.

FIG. 8 is a schematic diagram illustrating an example of a semiconductor detector module implemented as a multi-chip module according to an exemplary embodiment. This example shows how the semiconductor sensor also can have the function of substrate (A) in a Multi-Chip Module (MCM). The signal is routed (B) from the pixels (C) to inputs of parallel processing integrated circuits (e.g. ASICs) (D) which are positioned next to the active sensor area. It should be understood that the term Application Specific Integrated Circuit (ASIC) is to be interpreted broadly as any general integrated circuit used and configured for a specific application. The ASICs process the electric charge generated from each x-ray and converts it to digital data which can be used to estimate the energy. The ASICs are configured for connection a digital data processing circuitry so the digital data may be sent to further digital data processing (E) and memories located outside of the MCM and finally the data will be the input to the reconstructed image.

By way of example, in the ASICs the signal from each x-ray is measured and the deposited energy by each x-ray is estimated. The measured energy of each x-ray will be used to increase the contrast of desired elements in the image. To achieve this, energy information will be used to separate electronic noise from x-rays which Compton scatters in the semiconductor sensor from x-rays which react through photo effect. The information will preferably be weighted together to maximize the contrast for desired elements and structures in the object. There will also be some energy information from the measurement of the depth of interaction for the x-ray, which is performed since may keep track of which depth segment the x-ray converted. This is particularly important for the Compton scattered x-rays in the detector since for these x-rays the energy will be more uncertain since only a part of the original energy was deposited in the semiconductor sensor.

Figure 9:
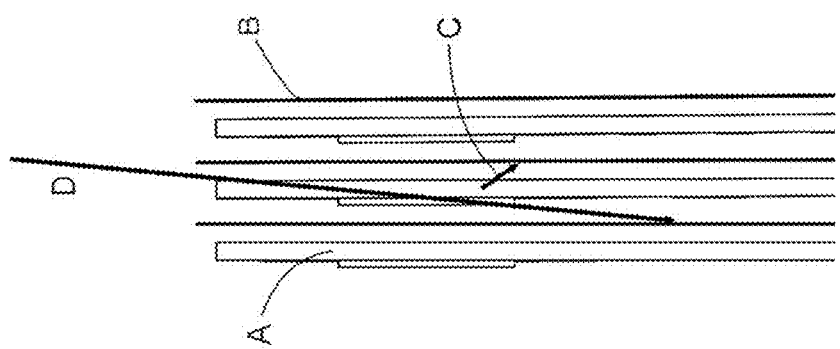
FIG. 9 is a schematic diagram illustrating an example of how several semiconductor detector modules can be positioned next to each other in order to build a whole x-ray detector.

FIG. 9 is a schematic diagram illustrating an example of how several semiconductor detector modules can be positioned next to each other in order to build a whole x-ray detector. In this particular example, several Multi Chip Modules (MCMs) (A) are positioned next to each other in order to build a whole x-ray detector. The MCMs are interfolded by anti-scatter foils, e.g. sheets of a heavy element (such as Tungsten), (B) in order to absorb x-rays which were Compton scattered in the semiconductor sensors (C) or in the object (D), these x-rays would otherwise contribute to the noise in the image. In other words, anti-scatter foils are placed between the individual sensors and work as x-ray collimators. Due to the lower acceptance angle for a bottom segment when compared to a segment located higher up, the detected object scatter will me lower for bottom segments. The difference in scatter counts between the layers can be used to estimate the scatter of each segment.

Figure 10:
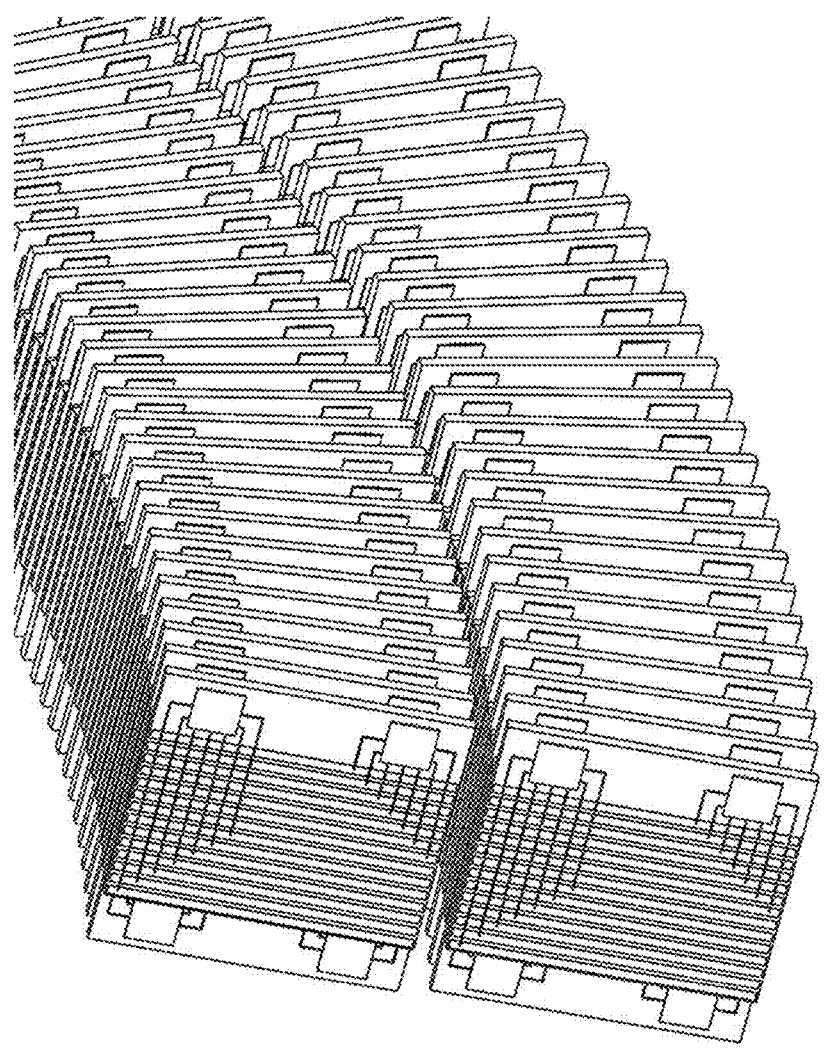
FIG. 10 is a magnified view illustrating an example of an arrangement of semiconductor detector modules in two layers.

FIG. 10 is a magnified view illustrating an example of an arrangement of semiconductor detector modules in two layers.

The methods of the present invention described herein may be implemented in corresponding devices.

According to a ninth aspect, there is provided a device for estimating object scatter in a photon-counting x-ray detector having at least two layers of detector diodes mounted in an edge-on geometry or at least two layers of diode segments of diodes segmented in the direction of the incoming x-rays, wherein said device is configured to estimate the object scatter contribution to the counts in a top layer of said at least two layers based on difference(s) in counts between the top layer and lower layer(s) under the assumption that object scatter has a slowly varying spatial distribution.

According to a tenth aspect, there is provided a device for estimating internal scatter of a photon-counting x-ray detector having at least two layers of detector diodes mounted in an edge-on geometry or at least two layers of diode segments of diodes segmented in the direction of the incoming x-rays, wherein said device is configured to estimate counts from reabsorption of photons that have Compton scattered inside the detector based on measuring counts in detector elements having a highly attenuating beam stop placed on top of the detector elements, in lower layer(s) or in both top layer and lower layer(s).

According to an eleventh aspect, there is provided a device for adjusting measured counts in a layered photon-counting x-ray detector having at least two layers of detector diodes mounted in an edge-on geometry or at least two layers of diode segments of diodes segmented in the direction of the incoming x-rays, wherein said device comprises a device of the ninth aspect.

According to a twelfth aspect, there is provided a device for adjusting measured counts in a layered photon-counting x-ray detector having at least two layers of detector diodes mounted in an edge-on geometry or at least two layers of diode segments of diodes segmented in the direction of the incoming x-rays, wherein said device comprises a device of the tenth aspect.

According to a thirteenth aspect, there is provided a device for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays, wherein said device comprises a device of the ninth aspect.

According to a fourteenth aspect, there is provided a device for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays, wherein said device comprises a device of the tenth aspect.

Figure 6:
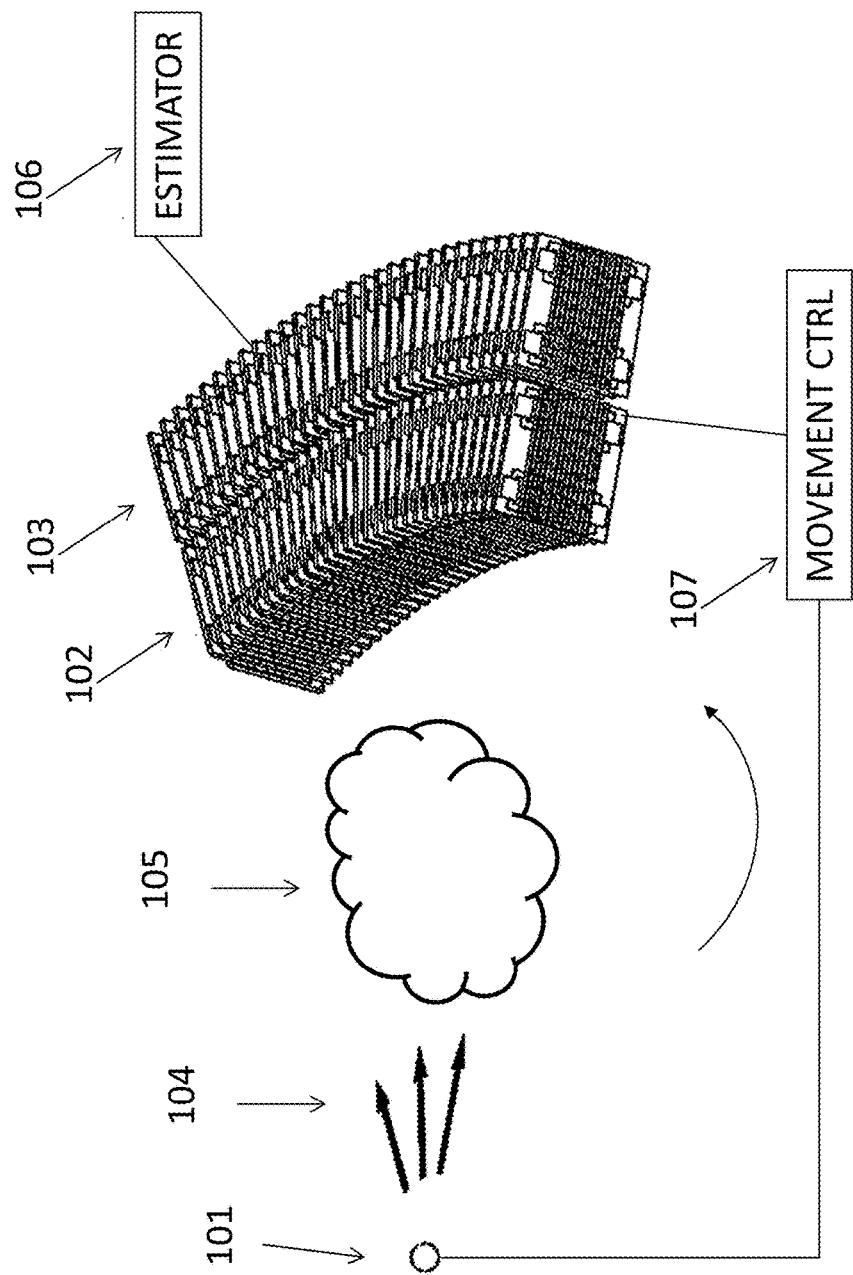
FIG. 6 is a schematic illustration of an embodiment of a device for x-ray tomographic imaging of an object.

In a particular embodiment, illustrated in FIG. 6, a device for x-ray tomographic imaging of an object while correcting for scatter comprise a source 101 of x-ray radiation 104 and a detector composed of two layers 102, 103 of direct conversion semiconductor diodes pointing back to the source. There is a spacing between individual diodes in both the top and bottom layer that corresponds to the diode width, and a displacement of the bottom layer in the rotational direction such that primary x rays missing the top layer diodes pass unattenuated to the lower level diodes. The source 101 and detector 102, 103 are arranged to be moved around the object obtaining projection x-ray images at different rotation angles, controlled by a movement controller 107. The arrangement comprises an estimator 106, connected to the detector and arranged for obtaining measurement data from the detector. The estimator may also be an integrated part of the detector. The estimator 106 is configured for, for each rotation angle, estimating the distribution of object scatter on the top layer of the detector, using the fact that the lower layer of the detector is shielded from object scatter by virtue of the top layer functioning like an anti-scatter grid with very high aspect ratio.

The estimator 106 is configured for performing the estimation according to the following steps. For each detector element in the top row, the corresponding measurement from the bottom row, displaced one diode width in direction of rotation, is subtracted after weighting to adjust for any difference in mean detection efficiency, for instance stemming from shadowing. The low spatial frequency representation of the difference is determined by means of low pass filtering or fitting of a parametric surface. This low frequency representation is an estimate of the object scatter distribution across the entire top layer. The approximation that internal detector scatter is a constant fraction $\gamma$ of the sum of the counts from primary and object scatter in a local neighborhood is used to estimate the scatter free signal in each top layer detector element by either subtracting said estimated object scatter in that element and dividing the difference by $(1+\gamma)$ to compensate for internal detector scatter; or to subtract a fraction $1/(1+\gamma)$ of the difference between measured counts and said estimated object scatter after low pass filtration from the difference between measured counts and said estimated object scatter itself. The scatter free signal in each bottom layer detector element is estimated by dividing the measured signal with $(1+\gamma)$; or by subtracting a fraction $1/(1+\gamma)$ of the low passed measured signal in that detector element from the measured signal in that detector element itself.

In a preferred embodiment, the semiconductor diodes are made of silicon.

In a preferred embodiment, the number of semiconductor diode layers exceed two. In other words, the number of semiconductor diode layers is greater than two.

In a preferred embodiment, the layers constitute segments in the direction of the incoming x-rays in a diode.

In another embodiment, a device for x-ray tomographic imaging of an object while correcting for scatter comprises a source of x-ray radiation and detector composed of two layers of direct conversion semiconductor diodes pointing back to the source. There is a spacing between individual diodes in both the top and bottom layer that corresponds to the diode width, and a displacement of the bottom layer in the rotational direction such that primary x rays missing the top layer diodes pass unattenuated to the lower level diodes. Beam stops are provided, covering less than 50% of all detector channels and distributed across the entire detector, both top and bottom layers, making them essentially blind to primary unscattered x-rays.

The source and detector are arranged to be moved around the object obtaining projection x-ray images at different rotation angles, controlled by a movement controller. The arrangement comprises an estimator, connected to the detector and arranged for obtaining measurement data from the detector. The estimator may also be an integrated part of the detector. The estimator is configured for, for each rotation angle, estimating the distribution of the sum of object and internal scatter of each layer is estimated by fitting a parametric surface to the counts of the detector elements with beam stops mounted on top of them. The estimated sum of object and internal scatter is subtracted from each detector element no covered with beam stops, thus obtaining an estimate of the scatter free signal of each detector element not covered with beam stops.

In a preferred embodiment, the semiconductor diodes are made of silicon.

In a preferred embodiment, the number of semiconductor diode layers exceed two. In other words, the number of semiconductor diode layers is greater than two.

In any of the devices described herein, anti-scatter elements, such as tungsten lamellae, may be mounted on the backside of each of a number of diodes.

It will be appreciated that the methods and devices described herein can be combined and re-arranged in a variety of ways.

Figure 7:
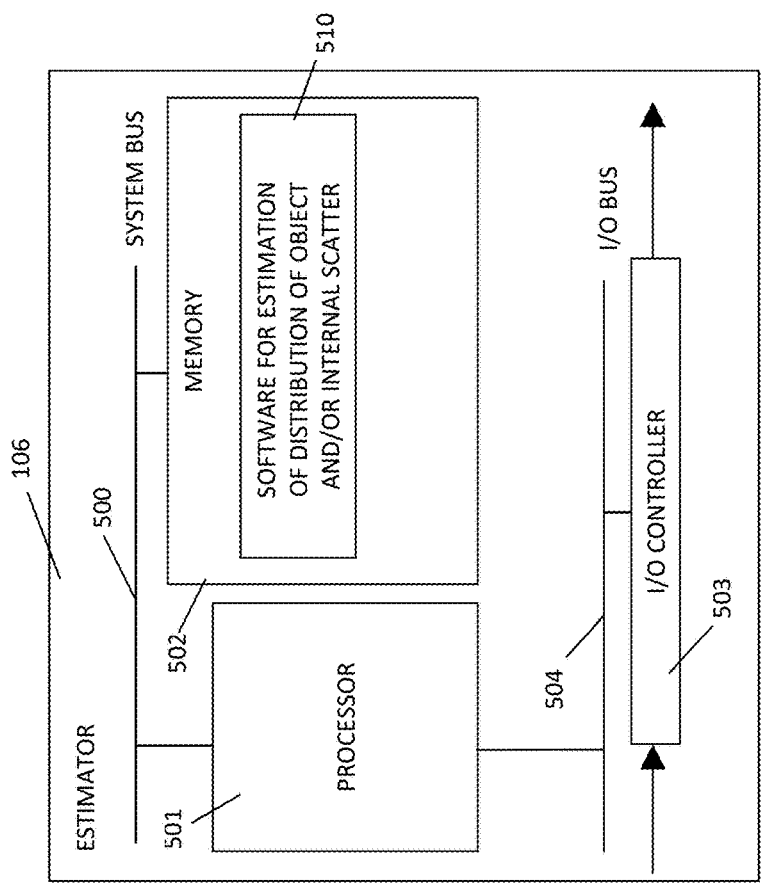
FIG. 7 is a schematic illustration of an embodiment of an estimator correcting for scatter.

For example, embodiments may be implemented in hardware, or in software for execution by suitable processing circuitry, or a combination thereof. An embodiment of an estimator is illustrated in FIG. 7.

The steps, functions, procedures, modules and/or blocks described herein may be implemented at least partly in hardware using any conventional technology, such as discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

In this particular example, at least some of the steps, functions, procedures, modules and/or blocks described herein are implemented in a computer program (software) 510, which is loaded into the memory 502 for execution by processing circuitry including one or more processors 501. The processor(s) 501 and memory 502 are interconnected via a system bus 500 to each other to enable normal software execution. An optional input/output device 503 may also be interconnected to the processor(s) 501 and/or the memory 502 via an I/O bus 504 to enable input and/or output of relevant data such as input parameter(s) and/or resulting output parameter(s).

By way of example, there is provided a computer program 510 for estimating, when executed by a processor 501, object scatter in a photon-counting x-ray detector having at least two layers of detector diodes mounted in an edge-on geometry or at least two layers of diode segments of diodes segmented in the direction of the incoming x-rays, wherein said computer program 510 comprises instructions, which when executed by the processor 501, cause the processor to estimate the object scatter contribution to the counts in a top layer of said at least two layers based on difference(s) in counts between the top layer and lower layer(s) under the assumption that object scatter has a slowly varying spatial distribution.

According to another example, there is provided a computer program 510 for estimating, when executed by a processor 501, internal scatter of a photon-counting x-ray detector having at least two layers of detector diodes mounted in an edge-on geometry or at least two layers of diode segments of diodes segmented in the direction of the incoming x-rays, wherein said computer program 510 comprises instructions, which when executed by the processor 501, cause the processor to estimate counts from reabsorption of photons that have Compton scattered inside the detector based on measurements of counts in detector elements having a highly attenuating beam stop placed on top of the detector elements, in lower layer(s) or in both top layer and lower layer(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

By way of example, the software or computer program may be realized as a computer program product, which is normally carried or stored on a computer-readable medium, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

The flow diagram or diagrams presented herein may at least partly be regarded as a computer flow diagram or diagrams, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively it is possibly to realize the modules predominantly by hardware modules, or alternatively by hardware. The extent of software versus hardware is purely implementation selection.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

REFERENCES

1. U.S. Pat. No. 6,618,466 B1 "Apparatus and method for x-ray scatter reduction and correction for fan beam CT and cone beam volume CT"
2. U.S. Pat. No. 8,183,535 B2 "Silicon detector assembly for X-ray imaging"
3. Roessl and Proksa in "K-edge imaging in x-ray computed tomography using multi-bin photon counting detectors", Physics in Medicine and Biology, vol 52, pp. 4679-96, 2007
4. Zhu, Bennett and Fahrig, "Scatter correction method for x-ray CT using primary modulation: theory and preliminary results" in IEEE Transactions of Medical Imaging, vol 25, pp. 1573-1587, 2006
5. Bornefalk, Persson and Danielsson, "Allowable forward model misspecification for accurate basis decomposition in a silicon detector based spectral CT" in IEEE Transactions of Medical Imaging vol. 34, pp. 788-795, 2015
6. Bornefalk and Danielsson, "Photon-counting spectral computed tomography using silicon strip detectors: a feasibility study", Physics in Medicine and Biology, vol. 55, pp. 1999-2022, 2010

The invention claimed is:

1. A method for estimating object scatter in a photon-counting x-ray detector having at least two layers of detector diodes mounted in an edge-on geometry or at least two layers of diode segments of diodes segmented in the direction of the incoming x-rays,
   the method comprising estimating the object scatter contribution to the counts in a top layer of said at least two layers based on difference(s) in counts between the top layer and lower layer(s) under the assumption that object scatter has a slowly varying spatial distribution.

2. The method of claim 1, wherein the estimation is performed for each of a number of projections during rotation of a gantry of a computed tomography system.

3. The method of claim 1, wherein the x-ray detector is a direct conversion x-ray detector using a direct-converter material.

4. A method for adjusting measured counts in a layered photon-counting x-ray detector having at least two layers of detector diodes mounted in an edge-on geometry or at least two layers of diode segments of diodes segmented in the direction of the incoming x-rays,
   the method comprising adjusting the measured counts at least partly based on the object scatter estimated according to claim 1, to thereby obtain unbiased estimates of the counts due to primary x-ray interactions.

5. The method of claim 4, wherein the measured counts are adjusted based on the estimated object scatter and a constant $\gamma$, which relates internal detector scatter as a constant fraction $\gamma$ of the sum of the counts from primary x-ray interactions and object scatter in a local neighborhood.

6. A method for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays,
   the method comprising performing the estimation at least partly based on the object scatter estimated according to claim 1.

7. A method for x-ray tomographic imaging of an object while correcting for scatter, wherein said method comprises:
providing a source of x-ray radiation and detector comprising two layers of direct conversion semiconductor diodes pointing back to the source, wherein a spacing between individual diodes is provided in both a top and bottom layer that corresponds to the diode width, and a displacement of the bottom layer in the rotational direction such that primary x-rays missing the top layer diodes pass unattenuated to the lower level diodes;
moving the source and detector around the object obtaining projection x-ray images at different rotation angles;
detecting radiation from the source by the detector; and
estimating, for each rotation angle, the distribution of object scatter on the top layer of the detector based on the fact that the lower layer of the detector is shielded from object scatter by virtue of the top layer functioning like an anti-scatter grid with very high aspect ratio.

8. The method of claim 7, wherein:
for each detector element in the top row, the corresponding measurement from the bottom row, displaced one diode width in direction of rotation, is subtracted after weighting to adjust for any difference in mean detection efficiency, for instance stemming from shadowing,
the low spatial frequency representation of the difference is determined by means of low pass filtering or fitting of a parametric surface, wherein this low frequency representation is an estimate of the object scatter distribution across the entire top layer,
the approximation that internal detector scatter is a constant fraction $\gamma$ of the sum of the counts from primary and object scatter in a local neighborhood is used to estimate the scatter free signal in each top layer detector element by:
subtracting said estimated object scatter in that element and dividing the difference by $(1+\gamma)$ to compensate for internal detector scatter, or
subtracting a fraction $1/(1+\gamma)$ of the difference between measured counts and said estimated object scatter after low pass filtration from the difference between measured counts and said estimated object scatter itself; and
the scatter free signal in each bottom layer detector element is estimated by:
dividing the measured signal with $(1+\gamma)$, or
subtracting a fraction $1/(1+\gamma)$ of the low passed measured signal in that detector element from the measured signal in that detector element itself.

9. A device for estimating object scatter in a photon-counting x-ray detector having at least two layers of detector diodes mounted in an edge-on geometry or at least two layers of diode segments of diodes segmented in the direction of the incoming x-rays,
wherein said device is configured to estimate the object scatter contribution to the counts in a top layer of said at least two layers based on difference(s) in counts between the top layer and lower layer(s) under the assumption that object scatter has a slowly varying spatial distribution.

10. A device for adjusting measured counts in a layered photon-counting x-ray detector having at least two layers of detector diodes mounted in an edge-on geometry or at least two layers of diode segments of diodes segmented in the direction of the incoming x-rays, wherein said device comprises a device of claim 9.

11. A device for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays, wherein said device comprises a device of claim 9.

12. A device for x-ray tomographic imaging of an object while correcting for scatter, wherein said device comprises:
a source of x-ray radiation and a detector comprising two layers of direct conversion semiconductor diodes pointing back to the source,
wherein there is a spacing between individual diodes in both a top and bottom layer that corresponds to the diode width, and a displacement of the bottom layer in the rotational direction such that primary x-rays missing the top layer diodes pass unattenuated to the lower level diodes,
wherein the source and detector are arranged to be moved around the object obtaining projection x-ray images at different rotation angles, controlled by a movement controller; and
an estimator, connected to the detector and arranged for obtaining measurement data from the detector, or being an integrated part of the detector, wherein the estimator is configured for estimating, for each rotation angle, the distribution of object scatter on the top layer of the detector, using the fact that the lower layer of the detector is shielded from object scatter by virtue of the top layer functioning like an anti-scatter grid with very high aspect ratio.

13. The device of claim 12, wherein the estimator is configured for performing the estimation according to the following:
for each detector element in the top row, the corresponding measurement from the bottom row, displaced one diode width in direction of rotation, is subtracted after weighting to adjust for any difference in mean detection efficiency, for instance stemming from shadowing;
the low spatial frequency representation of the difference is determined by means of low pass filtering or fitting of a parametric surface, wherein this low frequency representation is an estimate of the object scatter distribution across the entire top layer;
the approximation that internal detector scatter is a constant fraction $\gamma$ of the sum of the counts from primary and object scatter in a local neighborhood is used to estimate the scatter free signal in each top layer detector element by either subtracting said estimated object scatter in that element and dividing the difference by $(1+\gamma)$ to compensate for internal detector scatter, or subtracting a fraction $1/(1+\gamma)$ of the difference between measured counts and said estimated object scatter after low pass filtration from the difference between measured counts and said estimated object scatter itself; and
the scatter free signal in each bottom layer detector element is estimated by dividing the measured signal with $(1+\gamma)$, or by subtracting a fraction $1/(1+\gamma)$ of the low passed measured signal in that detector element from the measured signal in that detector element itself.

14. A computer-program product comprising a non-transitory computer-readable medium having stored thereon a computer program for estimating, when executed by a processor, object scatter in a photon-counting x-ray detector having at least two layers of detector diodes mounted in an edge-on geometry or at least two layers of diode segments of diodes segmented in the direction of the incoming x-rays, wherein said computer program comprises instructions, which when executed by the processor, cause the processor to estimate the object scatter contribution to the counts in a top layer of said at least two layers based on difference(s) in counts between the top layer and lower layer(s) under the assumption that object scatter has a slowly varying spatial distribution.

15. A method for estimating internal scatter of a photon-counting x-ray detector having at least two layers of detector diodes mounted in an edge-on geometry or at least two layers of diode segments of diodes segmented in the direction of the incoming x-rays,
the method comprising estimating counts from reabsorption of photons that have Compton scattered inside the detector based on selectively blinding some detector elements from primary radiation by placing a highly attenuating beam stop on top of the detector elements, in lower layer(s) or in both top layer and lower layer(s), and measuring the counts in those detector elements.

16. The method of claim 15, wherein the estimation is performed for each of a number of projections during rotation of a gantry of a computed tomography system.

17. The method of claim 15, wherein the x-ray detector is a direct conversion x-ray detector using a direct-converter material.

18. A method for adjusting measured counts in a layered photon-counting x-ray detector having at least two layers of detector diodes mounted in an edge-on geometry or at least two layers of diode segments of diodes segmented in the direction of the incoming x-rays,
the method comprising adjusting the measured counts at least partly based on the internal scatter estimated according to claim 15, to thereby obtain unbiased estimates of the counts due to primary x-ray interactions.

19. A method for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays,
the method comprising performing the estimation at least partly based on the internal scatter estimated according to claim 15.

20. A method for x-ray tomographic imaging of an object while correcting for scatter, wherein said method comprises:
providing a source of x-ray radiation and detector comprising two layers of direct conversion semiconductor diodes pointing back to the source, wherein a spacing between individual diodes is provided in both a top and bottom layer that corresponds to the diode width, and a displacement of the bottom layer in the rotational direction such that primary x-rays missing the top layer diodes pass unattenuated to the lower level diodes;
providing beam stops, covering less than 50% of all detector channels and distributed across the entire detector, in the bottom layer or both the top and bottom layers, making them essentially blind to primary unscattered x-rays;
moving the source and detector around the object obtaining projection x-ray images at different rotation angles;
detecting radiation from the source by the detector;
estimating, for each rotation angle, the distribution of the sum of object and internal scatter of each layer by fitting a parametric surface to the counts of the detector elements with beam stops mounted on top of them; and
subtracting the estimated sum of object and internal scatter from each detector element not covered with beam stops, thus obtaining an estimate of the scatter free signal of each detector element not covered with beam stops.

21. A device for estimating internal scatter of a photon-counting x-ray detector having at least two layers of detector diodes mounted in an edge-on geometry or at least two layers of diode segments of diodes segmented in the direction of the incoming x-rays,
wherein said device is configured to estimate counts from reabsorption of photons that have Compton scattered inside the detector based on measuring counts in detector elements having a highly attenuating beam stop placed on top of the detector elements, in lower layer(s) or in both top layer and lower layer(s).

22. A device for adjusting measured counts in a layered photon-counting x-ray detector having at least two layers of detector diodes mounted in an edge-on geometry or at least two layers of diode segments of diodes segmented in the direction of the incoming x-rays, wherein said device comprises a device of claim 21.

23. A device for estimating the total amount and spatial profile of scattered radiation absorbed in a layered photon-counting x-ray detector having at least two layers of detector diodes mounted in an edge-on geometry or at least two layers of diode segments of diodes segmented in the direction of the incoming x-rays, wherein said device comprises a device of claim 21.

24. A device for x-ray tomographic imaging of an object while correcting for scatter, wherein said device comprises:
a source of x-ray radiation and detector comprising two layers of direct conversion semiconductor diodes pointing back to the source,
wherein there is a spacing between individual diodes in both a top and bottom layer that corresponds to the diode width, and a displacement of the bottom layer in the rotational direction such that primary x-rays missing the top layer diodes pass unattenuated to the lower level diodes,
wherein beam stops are provided, covering less than 50% of all detector channels and distributed across the entire detector, in the bottom layer or both the top and bottom layers, making them essentially blind to primary unscattered x-rays;
wherein the source and detector are arranged to be moved around the object obtaining projection x-ray images at different rotation angles, controlled by a movement controller; and
an estimator, connected to the detector and arranged for obtaining measurement data from the detector, or being an integrated part of the detector, wherein the estimator is configured for estimating, for each rotation angle, the distribution of the sum of object and internal scatter of each layer by fitting a parametric surface to the counts of the detector elements with beam stops mounted on top of them, and the estimated sum of object and internal scatter is subtracted from each detector element not covered with beam stops, thus obtaining an estimate of the scatter free signal of each detector element not covered with beam stops.

25. A computer-program product comprising a non-transitory computer-readable medium having stored thereon a computer program for estimating, when executed by a processor, internal scatter of a photon-counting x-ray detector having at least two layers of detector diodes mounted in an edge-on geometry or at least two layers of diode segments of diodes segmented in the direction of the incoming x-rays,
wherein said computer program comprises instructions, which when executed by the processor, cause the processor to estimate counts from reabsorption of photons that have Compton scattered inside the detector based on measurements of counts in detector elements having a highly attenuating beam stop placed on top of the detector elements, in lower layer(s) or in both top layer and lower layer(s).

* * * * *